United States Patent [19]

Takematsu et al.

[11] Patent Number: 4,622,060
[45] Date of Patent: Nov. 11, 1986

[54] HERBICIDAL COMPOSITIONS AND HERBICIDAL PROCESSES

[75] Inventors: Tetsuo Takematsu; Makoto Konnai, both of Utsunomiya; Kunitaka Tachibana, Yokohama; Takashi Tsuruoka, Kawasaki; Shigeharu Inouye; Tetsuro Watanabe, both of Yokohama, all of Japan

[73] Assignee: Meiji Seika Kaisha, Ltd., Tokyo, Japan

[21] Appl. No.: 718,341

[22] Filed: Apr. 1, 1985

Related U.S. Application Data

[60] Continuation-in-part of Ser. No. 495,819, May 18, 1983, Pat. No. 4,552,584, which is a division of Ser. No. 164,510, Jul. 2, 1980, abandoned, which is a division of Ser. No. 959,838, Nov. 13, 1978, Pat. No. 4,309,208.

[30] Foreign Application Priority Data

Mar. 9, 1978 [JP] Japan .................................. 53-25971

[51] Int. Cl.$^4$ ...................... A01N 47/30; A01N 57/20
[52] U.S. Cl. ............................................. 71/86; 71/120
[58] Field of Search .................................. 71/86, 120

[56] References Cited

U.S. PATENT DOCUMENTS 4,032,324 6/1977 Faust et al. ............................ 71/120
4,382,812 5/1983 Takematsu et al. .................... 71/86

OTHER PUBLICATIONS

Kando et al, "New Antibiotic SF-1293, etc.," (1973), CA 81:89705b (1974).
Hirano et al, "Synergistic Herbicidal, etc.," (1975), CA 84:100861j (1976).
Pirvescu, "Herbicide Testing for Weed, etc.," (1978), CA 89:101722e (1978).
Bosch et al, "Chlorinated N-phenyl-, etc.," (1975), CA 83:127506p.
Badische, "Herbicidal Compositions," (1972), CA 78:12695d.
Shipman, "Soil-applied Herbicides, etc.," (1974), CA 80:117063r (1974).

*Primary Examiner*—Glennon H. Hollrah
*Assistant Examiner*—Robert Lelkes
*Attorney, Agent, or Firm*—Larson and Taylor

[57] ABSTRACT

A known antibiotic, SF-1293 substance and salts thereof have now been found to exhibit high herbicidal effects against a wide variety of herbaceous and woody plants, but they are non-phytotoxic particularly to a useful woody plant, *Chamaecyparis obtusa*. The herbicidal effects of these SF-1293 substances can be synergistically enhanced by applying in combination with herbicides selected from Linuron, Monolinuron, Monuron and Diuron each known as herbicides of urea derivative class.

6 Claims, No Drawings

HERBICIDAL COMPOSITIONS AND HERBICIDAL PROCESSES

CROSS-REFERENCE TO RELATED APPLICATIONS

This application is a continuation-in-part application based on pending U.S. patent application Ser. No. 495,819 filed May 18, 1983, now U.S. Pat. No. 4,552,584 which is a divisional application from a U.S. patent application Ser. No. 164,510 filed July 2, 1980, now abandoned, which is, in turn, a divisional application of U.S. patent application Ser. No. 959,838 filed Nov. 13, 1978, now U.S. Pat. No. 4,309,208. There are also a U.S. patent application Ser. No. 334,042 filed Dec. 23, 1981, now U.S. Pat. No. 4,448,601, filed as a continuation application of said U.S. patent application Ser. No. 959,838; and a U.S. patent application Ser. No. 263,454 filed May 15, 1981, now a U.S. Pat. No. 4,455,163, filed as a divisional application of said U.S. patent application Ser. No. 959,838, now U.S. Pat. No. 4,309,208.

BACKGROUND OF THE INVENTION

1. Field of the Invention

This invention relates to herbicidal compositions, and processes of controlling unwanted plants using the herbicidal compositions.

2. Description of the Prior Art

All of the active substances which have hitherto been used as herbicide are the chemically synthetic compounds, which may sometime give rise to problems of environmental pollution. From a viewpoint of increasingly severe legal regulations of environmental pollution, the demand now increases to provide those herbicidal substances which can be rapidly decomposed in the surrounding conditions and cause no environmental contamination.

We described and claimed the antibiotic, SF-1293 substance and a microbiological process for the production thereof (see Japanese Pat. No. 827,768, U.S. Pat. No. 3,832,394 and German Pat. No. 2,236,599). It is now found that the SF-1293 substance as a herbicide can meet the requirements mentioned above since it is susceptible to metabolism and breakdown into harmless substances in the course of the material-circulation occurring in nature.

The SF-1293 substance (in the free acid form) is the compound of the formula:

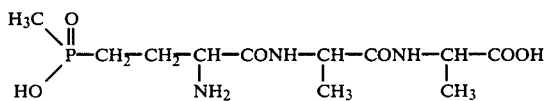

As described in the aforesaid U.S. and German patents, the SF-1293 substance is highly active to various fungal diseases of plants, including *Pellicularia sasakii* (sheath blight on rice) and *Piricularia oryzae* (rice blast).

SUMMARY OF THE INVENTION

As a result of our further study of the biological activities and utilities of the SF-1293 substance, we have now found that it exhibits a considerably high herbicidal effect when applied at a rate of about ten times higher than that at which it has been used as fungicide. Thus, it has been found that the SF-1293 substance, and various salts thereof are herbicidally active to growing annual and perennial weeds as well as various bushes and trees, and that upon foliage treatment, they can severely damage or kill the overground segments of the plants and strongly inhibit regrowth of the plants from their underground rhizomes.

The SF-1293 substance (the free acid form) and salts thereof (hereinafter collectively referred to as merely "SF-1293 substances") are effective to severely damage or kill unwanted plants both when applied directly to the plants ("post-emergence application") and when applied to soil or other growth medium where the plants are growing, to prevent the emergence of seedlings of the plants ("pre-emergence application").

The SF-1293 substances for use in this invention are advantageous in that they may be applied at an optional time in all seasons and that they are effective not only as a contact herbicide but also as a translocated or systemic herbicide. Further, they have favorably the unique feature that they are non-phytotoxic to useful woody plant, *Chamaecyparis obtusa* (Japan cypress, "hinoki" in Japanese, which provides a wood material extensively used in the construction of furnitures and houses) but they are highly toxic to unwanted bushes and weeds growing in the area where the useful woody plants occur naturally or are cultivated artificially.

In recent years, infestation of exotic and naturalized weeds and perennial weeds comes into question, and N-phosphonomethylglycin (which is usually known as glyphosate) is effectively used to control the growth of these weeds. It has been observed that the antibiotic SF-1293 substance, which acts similarly to glyphosate, is very superior to glyphosate in respect of the herbicidal properties and weed-control spectrum. Thus, as compared with the glyphosate, the SF-1293 substance is effective at a lower concentration, more rapidly develops the herbicidal effect and shows a much wider spectrum of weed control, and further it is absolutely non-phytotoxic towards *Chamaecyparis obtusa* as already stated. In contrast, glyphosate disadvantageously shows a phytotoxicity to *Chamaecyparis obtusa*. Besides, glyphosate is much less active to broadleaved weeds and perennial weeds such as *Rumex japonicus* and *Cayratia japonica*. While, the SF-1293 substance is equivalently active against the weeds irrespective of weed species at the same application rate and completely suppresses regrowth or recovery of perennial weeds.

Generally, non-crop land, orchard, forestry land and grassland can be infested with annual and perennial weeds and various bushes. In order to control the growth thereof, either treatment of applying a mixture of two or more herbicides at once or treatment of applying different or same herbicide(s) several times at intervals may be employed. Both of these herbicidal procedures, however, arey very complicated and disadvantageous in the cost and labor involved therein. The SF-1293 substances are highly active against almost all weeds, bushes and trees except for *Chamaecypairs obtusa*, so that application of the SF-1293 substances alone can control all of the undesired plants, inclusive of weeds and unwanted trees, as intended. Besides, the SF-1293 substances can prevent regrowth or recovery of the undesired plants, indicating that they are a herbicide of particular great value in practice. Thus, the SF-1293 substances are effectively applied for land preparation in forestry land, control of bottom weeds growing in forestry land of *Chamaecyparis obtusa*, control of weeds and bushes in grassland, bottom weed-control in orchard and inhibition of weed growth in non-crop land, and further they are suitable for pre-sowing treatment in uncultivated upland, by utilizing their properties that they will become inactivated at a relatively high rate in soil. The SF-1293 substances are also suitable for "spot" herbicidal treatment in crop area or lawn area infested with vicious perennial weeds.

The SF-1293 substances for use in the invention may alone be applied in the form of a herbicidal formulation comprising the SF-1293 substances as the active ingredient which is mixed with a liquid or solid diluent or carrier.

Said herbicidal formulation may generally comprise as the active ingredient the SF-1293 substances in an amount of 0.01% to 50% by weight of the formulation. When applied to the herbicidal treatment, this formulation may be diluted with water to a concentration of 0.05% to 5% with regard to the active ingredient.

The salts of the SF-1293 substance which may be an alkali metal salt, an alkaline earth metal salt, a divalent-metal salt, an unsubstituted or substituted ammonium salt or an acid-addition salt which is generally represented by the following formula:

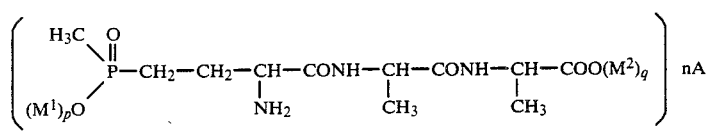

(I)

wherein $M^1$ and $M^2$, which may be the same or different, each represents hydrogen atom or a cation selected from sodium, potassium, lithium, copper, magnesium, calcium, zinc, nickel and manganese, or an ammonium cation either unsubstituted or substituted by one, two, three or four lower alkyl, hydroxy-lower alkyl, particularly hydroxyethyl or lower alkenyl group; A represents an inorganic or organic acid selected from hydrochloric, sulfuric, hydrobromic, phosphoric, perchloric, nitric, acetic, propionic, citric, tartaric, monochloroacetic, trichloroacetic and trifluoroacetic acids; and n is 0, ½ or 1, p is the inverse number of the valency of $M^1$, and q is the inverse number of the valency of $M^2$.

Said herbicidal formulation may be in the form of aqueous solution, wettable powder, dusting powder, emulsion, granules or grains comprising the active ingredient in admixture with a suitable diluent or carrier.

The solid formulation may be in the form of dusting powders or granules. Suitable solid diluents include kaolin, clay, bentonite, kieselguhr, dolomite, calcium carbonate, talc, powdered magnesia, Fuller's earth, gypsum, Hewitt's earth, diatomaceous earth and vermiculite.

Solid formulation may also be in the form of dispersible powders or grains comprising a wetting agent to facilitate the dispersion in liquids of the powder or grains which may contain also fillers and suspending agents.

Liquid formulation include aqueous solutions, dispersions or emulsions which may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are acetone, isopropyl alcohol, propylene glycol, diacetone alcohol, benzene, toluene, kerosene, methylnaphthalene and cyclohexanone.

By including suitable additives, for example, additives for improving the distribution, adhesive power and resistance to rain on treated surfaces, the different formulation can be better adapted for intended purposes.

Said herbicidal formulations can comprise also other herbicides or plant-growth regulators known per se, for example, germination inhibitors so as to envisage enhancement of the herbicidal effect of the SF-1293 substances and extension of a period during which the substances remain active.

Said herbicidal formulations may also be in the form of liquid for use as sprays which are generally aqueous dispersions or emulsions containing the active ingredient in the presence of one or more wetting agent(s), dispersing agent(s), emulsifying agent(s) or suspending agent(s). These agents can be cationic, anionic, nonionic or ampholytic agents.

Suitable cationic agents are quaternary ammonium compounds, for example, cetyltrimethylammonium bromide and alkylpyridinium chloride. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates). Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable ampholytic agents are alkyldimethyl betaine and dodecylaminoethyl glycine. Suitable suspending agents are hydrophilic colloids (for example, polyvinylpyrrolidone and sodium carboxymethylcellulose), and the vegetable gums (for example, gum acacia and gum tragacanth).

The herbicidal formulation of the SF-1293 substances for use as aqueous dispersions or emulsions are generally supplied in the form of a concentrate containing a high proportion of the active ingredient, the concentrate being diluted with water before use. These concentrates often should be able to withstand storage for prolonged periods and after such storage be capable of dilution with water in order to form aqueous preparations which remain homogeneous for a sufficient time to enable them to be applied by conventional spray equipment.

The rate of application of the SF-1293 substances required to control unwanted plants will depend upon the identity of the plant species and the particular active compound selected for use as well as the climate conditions. However, in general, an application rate of 25 g. to 3000 g. per 10 ares is used. Our experiments have shown that it is most efficient for the herbicidal purpose to apply at a rate of about 100 l per 10 ares the liquid formulation containing 0.01% to 0.05% by weight of the active SF-1293 substance to weeds of less than 10 cm in height or the liquid formulation containing 0.05% to 0.2% by weight of the active SF-1293 substance to weeds of 10 to 30 cm in height.

As stated hereinbefore, the SF-1293 substances are effective not only as the contact herbicide but as the translocated or systemic herbicide, thereby achieving the regrowth-inhibitory effect which is most important for control of perennial weeds and bushes.

We have made further great endeavors to utilize the inherent, advantageous features of the SF-1293 substances to a maximum, and as a consequence we have discovered that the herbicidal effects of the SF-1293 substances can be appreciably improved when they are applied in combination with one or more known herbicides which are selected from Linuron, Monolinuron, Monuron and Diuron, each known as herbicides of urea derivative class.

Linuron, Monolinuron, Monuron and Diuron are herbicidal urea derivatives which are an N-(4-chloro- or 3,4-dichlorophenyl)-N'-methyl- or N'-methoxy-N'-methylurea represented by a general formula:

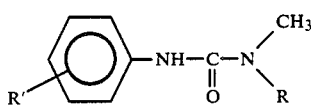

(II)

wherein R is a methyl group and R' is 4-chloro group for N-(4-chlorophenyl)-N',N'-dimethylurea (usually called "Monuron"); R is a methyl group and R' is 3,4-dichloro groups for N-(3,4-dichlorophenyl)-N',N'-dimethylurea (usually called "Diuron"); R is a methoxy group and R' is 4-chloro group for N-(4-chlorophenyl)-N'-methoxy-N'-methylurea (usually called "Monolinuron"); and R is a methoxy group and R' is 3,4-dichloro groups for N-(3,4-dichlorophenyl)-N'-methoxy-N'-methylurea (usually called "Linuron").

DETAILED DESCRIPTION OF THE INVENTION

According to an aspect of this invention, therefore, there is provided a herbicidal composition consisting essentially of a herbicidally effective amount of a mixture of:

(A) SF-1293 substance or an SF-1293 substance salt of the formula:

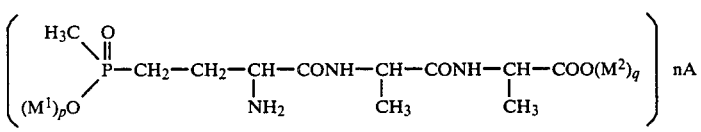

(I)

wherein $M^1$ and $M^2$ are each hydrogen or a cation selected from the group consisting of sodium, potassium, lithium, copper, magnesium, calcium, zinc, nickel, manganese and ammonium which is unsubstituted or substituted by 1-4 lower alkyl, hydroxy lower alkyl, or lower alkenyl; A is an inorganic or organic acid selected from the group consisting of hydrochloric, sulfuric, hydrobromic, phosphoric, perchloric, nitric, acetic, propionic, citric, tartaric, monochloroacetic, trichloroacetic and trifluoroacetic acids; n is 0, 0.5 or 1, p is the inverse number of the valency of $M^1$; and q is the inverse number of the valency of $M^2$; and (B) an N-(4-chloro- or 3,4-dichlorophenyl)-N'-methyl- or N'-methoxy-N'-methylurea which is selected from N-(3,4-dichlorophenyl)-N'-methoxy-N'-methylurea (i.e., Linuron), N-(4-chlorophenyl)-N'-methoxy-N'-methylurea (i.e., Monolinuron), N-(4-chlorphenyl)-N',N'-dimethylurea (i.e., Monuron), and N-(3,4-dichlorophenyl)-N',N'-dimethylurea (i.e., Diuron), in admixture with an inert carrier, the weight ratio of component (A) to component (B) being in the range of 1:3 to 3:1.

According to a second aspect of this invention, there is provided a process for severely damaging or killing unwanted herbaceous and bushy plants, which comprises applying to plants susceptible thereto or to the growth medium of said plants a herbicidally effective amount of a composition consisting essentially of a mixture of:

(A) SF-1293 substance or an SF-1293 substance salt of the formula:

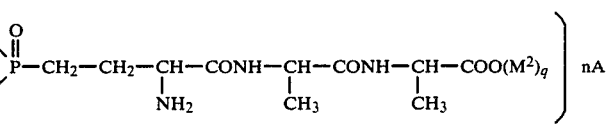

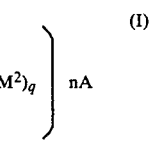

wherein $M^1$ and $M^2$ are each hydrogen or a cation selected from the group consisting of sodium, potassium, lithium, copper, magnesium, calcium, zinc, nickel, manganese and ammonium which is unsubstituted or substituted by 1-4 lower alkyl, hydroxy lower alkyl, or lower alkenyl; A is an inorganic or organic acid selected from the group consisting of hydrochloric, sulfuric, hydrobromic, phosphoric, perchloric, nitric, acetic, propionic, citric, tartaric, monochloroacetic, trichloroacetic and trifluoroacetic acids; n is 0, 0.5 or 1; p is the inverse number of the valency of $M^1$; and q is the inverse number of the valency of $M^2$, with (B) an N-(4-chloro- or 3,4-dichlorophenyl)-N'-methyl- or N'-methoxy-N'-methylurea which is selected from N-(3,4-dichlorophenyl)-N'-methoxy-N'-methylurea (i.e., Linuron), N-(4-chlorophenyl)-N'-methoxy-N'-methylurea (i.e., Monolinuron), N-(4-chlorophenyl)-N',N'-dimethylurea (i.e., Monuron), and N-(3,4-dichlorophenyl)-N',N'-dimethylurea (i.e., Diuron), in admixture with an inert carrier, the weight ratio of component (A) to component (B) being in the range of 1:3 to 3:1, to inhibit the growth of said unwanted plant.

According to a further aspect of this invention, there is provided a process for severely damaging or killing crab grass, pigweed, yellow foxtail, Orchard grass, smart weed, clover and bitter dock, which comprises applying the weed or the medium of growth of the weed a herbicidally effective amount of the composition consisting essentially of a mixture of (A) SF-1293 substance or a sodium salt thereof and (B) a herbicidal urea derivative selected from N-(3,4-dichlorophenyl)-N'-methoxy-N'-methylurea, N-(4-chlorophenyl)-N'-methoxy-N'-methylurea, N-(4-chlorophenyl)-N',N'-dimethylurea and N-(3,4-dichlorophenyl)-N',N'-dimethylurea, at a weight ratio of the component (A) to component (B) of 1:3 to 3:1 as active ingredient.

The salts of the SF-1293 substance which may be used in combination with the component (B) typically include those of the general formula (I) as defined hereinbefore and is preferably the mono-sodium salt, di-sodium salt, mono-ammonium salt or di-ammonium salt.

Our extensive studies on mixtures of the SF-1293 substances with the herbicidal urea derivatives of formula (II) have revealed the following:

Firstly, the herbicidal activity of the SF-1293 substances may be significantly enhanced when they are applied in combination with the herbicidal urea derivatives of formula (II).

By way of example, as will be seen from Table 6 given hereinbelow, application of 100 1/10 ares of a solution containing monosodium salt of the SF-1293 substance used alone at 0.05% concentration gives about 50% kill to *Rumex obtusifolius* (one of broad-leaved weeds) but cannot bring about suppression of regrowth of this weed, whereas application of 100 1/10 ares of a solution containing Linuron at 0.1% concentration allows only partial damage of the stem and foliage of *Rumex obtusifolius* but does not exhibit the effect of killing or suppression of regrowth of this weed. In contrast, the application of 100 1/10 ares of a solution containing in combination SF-1293 monosodium salt at 0.05% concentration and Linuron at 0.1% concentration achieves earlier development and pronounced enhancement of the herbicidal effect of the SF-1293 monosodium salt, resulting in complete kill of the overground segments but in no regrowth from the underground rhizomes of this weed. The same can be observed for *Zoysia japonica* which is one of graminaceous perennial weeds. Thus, application of a solution containing SF-1293 monosodoum salt at 0.1% concentration gives about 50% kill to *Zoysia japonica* but allows the regrowth to take place to an extent comparable to the untreated plot at the lapse of three months after the treatment. While, application of a solution containing Linuron at 0.1% concentration exhibits slight or substantially no activity to graminaceous plants. On the other hand, the application of a solution containing in combination 0.1% SF-1293 monosodium salt and 0.1% Linuron achieves complete kill and no regrowth whatsoever at the lapse of three months after treatment, owing to the synergistically increased activity of the SF-1293 sodium salt. Thus, the combined use of the SF-1293 substances and Linuron, a herbicidal urea derivative of formula (II) can lead to salient improvement in the contact and systemic, herbicidal activities of the SF-1293 substances towards both broad-leaved perennial weeds and graminaceous perennial weeds and bring about extremely improved effect of inhibiting the regrowth of the weeds.

Such noticeable improvements have been achieved also when Monolinuron, Monuron or Diuron known as one of the herbicidal urea derivatives is applied in combination with the SF-1293 substances, as illustrated in Examples 9-10.

Secondly, the SF-1293 substances exhibit a wider spectrum of weed control when they are applied in combination with the component (B) compounds, as shown in Examples 9-10. In order to ensure that the SF-1293 substances can achieve to the utmost the effect of inhibiting the regrowth of perennial weeds, it is necessary that they should translocate and migrate into the underground segments of the weed plant after foliage treatment but before killing of the foliage occurs. In the herbicidal treatment of plants such as *Calystegia hederacea* which are very susceptible of the contact herbicidal effect of the herbicide applied thereto, it is difficult to inhibit regrowth of this weed from the underground rhizomes due to that killing of the foliage takes place before the SF-1293 substances commmence their translocation and migration into the underground rhizomes. Nevertheless, the combined use of the SF-1293 substances and the component (B) compounds enhances the translocated herbicidal activity and thus strongly inhibits even regrowth of such plants as *Calystegia hederacea* because the combined use of the component (A) and (B) compounds can achieve the migration of the active agents into the underground rhizomes prior to killing of the foliage. All of the component (B) urea derivatives of formula (II) enable extension of weed-control spectra of the SF-1293 substances when they are applied in combination therewith.

The herbicidal compositions of this invention comprising a mixture of the SF-1293 substances and the urea derivative compounds (B) can be applied for various herbicidal purposes in many areas and lands including crop area, forestry land, grassland, orchard and non-crop land, as hereinbefore described for the herbicidal formulation comprising the SF-1293 substances alone as active ingredient. Further, the compositions of this invention may be applied in aquatic areas to control aquatic weeds and algae as well as in aquatic rice plant filed after the harvest of the ripened rice plants.

The ratio of the SF-1293 substances (A) to the urea derivative compounds (B) to be incorporated in the compositions may vary over a wide range depending upon the nature of the compounds (B) and the envisaged use of the compositions. By way of general guidance, however, the weight ratio of the SF-1293 substances to the compounds (B) may usually be in the range of 1:3 to 3:1.

The total amount or concentration of the SF-1293 substance (A) and the compound (B) in the herbicidal compositions of this invention is generally in a range of 0.5% to 80% by weight of the whole compositions. Upon use, the composition may usually be diluted to an active ingredient concentration of 0.05% to 0.5% by weight. The amount of the SF-1293 substance applied usually may then be in a range of 50 g to 200 g per 10 ares and preferably is in the range of 50 g to 150 g per 10 ares.

The compositions of this invention may be applied generally at a rate of 25 to 250 l, preferably 50 to 150 l of the SF-1293 substance per 10 ares.

The amount of the SF-1293 substances to be used in the composition of this invention to kill perennial weeds and bushes and to inhibit regrowth thereof will be affected also by the surrounding climatic conditions, for example, temperature and intensity of light. By way of example, however, the purposes envisaged can be attained by applying the SF-1293 substances at a rate of: 25 to 200 g per 10 ares for perennial weeds of 1 m or less in height (e.g. *Artemisia princeps, Rumex japonicus, Cy-*

*perus rotundus* etc.); 75 to 200 g/10 ares for perennial weeds of 1 m or more in height (e.g. *Sasa nipponica, Miscanthus sinensis* etc.) and small bushes (e.g. *Rhododendron haempferi, Rubus crategifolins* etc.); and 150 to 200 g/10 ares for big bushes (e.g. *Castanea crenata, Quercus serrata* etc.) as well as for control of fresh sprouts from big stumps.

The compositions of this invention can be formulated into any conventional form, including aqueous solution, dusting powder, wettable powder, emulsion, granule and grain using any known solid or liquid diluent or carrier by any convenient method, as described hereinbefore for the single use of the SF-1293 substance.

This invention is further illustrated but not limited by the following Examples in which percentages (%) are all by weight unless otherwise stated. In the examples mono-substituted salts of SF-1293 substance are essentially in the form of the corresponding phosphate (only $M^1$ in the above formula (I) is a cation and $M^2$ is a hydrogen atom).

Examples 1–3 illustrate the preparation of the compositions according to the invention.

EXAMPLE 1

Wettable Powder

| | |
|---|---|
| SF-1293 substance (free acid) | 10.0% |
| Linuron | 20.0% |
| Kieselguhr | 40.0% |
| Dodecylbenzenesulfonate (as surfactant) | 30.0% |

The ingredients listed above were together mixed uniformly in the proportions indicated and ground finely to prepare wettable powders, which are readily dispersible in water and used as, for example, sprays for foliage treatment.

EXAMPLE 2

Wettable Powder

| | |
|---|---|
| Mono-(diethanolamine) salt of SF-1293 substance | 15.0% |
| Monolinuron | 30.0% |
| Kieselguhr | 50.0% |
| Monosorbitan alkylester | 5.0% |

The ingredients listed above were together mixed uniformly in the proportions indicated and ground finely to prepare wettable powders, which are readily dispersible in water and used as, for example, sprays for foliage treatment.

EXAMPLE 3

Dusting Powder

| | |
|---|---|
| Mono-isopropylamine salt of SF-1293 substance | 5.0% |
| Monuron | 10.0% |
| Talc | 85.0% |

Compositions in the form of dusting powder were prepared by mixing and grinding uniformly all the ingredients listed above in the proportions stated. The dusting powder may directly be applied for foliage treatment at a rate of 0.4 to 6 kg per 10 ares.

Examples 4–8 illustrate the herbicidal properties of the SF-1293 substances.

EXAMPLE 4

(Pre-emergence Test)

Upland soil was placed in a pot of 10 cm diameter and seeds of *Digitaria adscendens* (Crabgrass) were sown in the soil at a depth of 1 cm. After gently pressing the soil surface, the soil was sprayed evenly with solutions of SF-1293 substance mono-sodium salt dissolved at different concentrations in 5 cc of water. 10 Days after spraying, the number of the seedlings of crabgrass was counted and percentage (%) of prevention of emergence was evaluated by comparison with untreated plots. For comparison, the tests were also conducted using glyphosate instead of the SF-1293 sodium salt. The results are shown in Table 1 below.

TABLE 1

| | Prevention (%) of Emergence Rate of Application g/10a | | | |
|---|---|---|---|---|
| Test Compounds | 0 | 100 | 250 | 500 |
| SF-1293 substance (mono-Na salt) | 0 | 95 | 100 | 100 |
| Glyphosate (isopropylamine salt) (Control) | 0 | 0 | 0 | 0 |

EXAMPLE 5

(Post-emergence Test)

Upland soil was placed in a pot of 10 cm diameter and seeds of crabgrass were sown in the soil at a depth of 1 cm from the soil surface. When the seedlings grew to a height of about 10 cm, 1.2 ml (equivalent to 100 l/10a) of aqueous solutions of the test compounds at different concentrations as indicated in Table 2 below were applied evenly for foliage treatment. 10 Days after treatment, damage to plants was visually assessed on a scale of 0 to 10 where 0 indicates no effect and 10 indicates complete kill.

The detail of this assessment made in this example was as follows:

| Scale | Foliage Damage (%) |
|---|---|
| 0 | 0% |
| 1 | 10% |
| 2 | 20% |
| 3 | 30% |
| 4 | 40% |
| 5 | 50% |
| 6 | 60% |
| 7 | 70% |
| 8 | 80% |
| 9 | 90% |
| 10 | 100% |

The test results are tabulated in Table 2.

TABLE 2

| | Damage Scale Concentration (ppm) | | | |
|---|---|---|---|---|
| Test Compound | 0 | 0.01 | 0.03 | 0.1 |
| SF-1293 substance (mono-Na salt) | 0 | 1 | 8 | 10 |
| SF-1293 substance (dimethylamine salt) | 0 | 3 | 10 | 10 |
| Glyphosate (isopropylamine salt) (Control) | 0 | 0 | 5 | 10 |

The above table shows that an improved herbicidal effect is exhibited by an organic amine salt of SF-1293 substance.

EXAMPLE 6

Aqueous solutions containing sodium salt of SF-1293 substance at different concentrations as indicated in Table 3 below and 0.1% of octylphenylpolyoxyethanol as surfactant were prepared and applied at a rate of 150 l per 10 ares directly to spontaneously occurring perennial weeds at growth stages indicated in Table 3. 7 Days and 14 days after foliage treatment, damage to the plants was visually assessed on a scale of 0 to 5 where 0 signifies no effect and 5 signifies complete kill.

The detail of this assessment made in this example was as follows:

| Scale | Foliage Damage (%) |
|---|---|
| 0 | 0 |
| 1 | 20% |
| 2 | 40% |
| 3 | 60% |
| 4 | 80% |
| 5 | 100% |

One month after treatment, evaluation was made for inhibition of regrowth expressed in terms of symbols ranging from (−) to (+++) where (−) means no regrowth, namely complete suppression of regrowth, (±) remarkable suppression of regrowth; (+) considerable suppression of regrowth; (++) medium suppression of regrowth; and (+++) no suppression of regrowth.

The results are set forth in Table 3.

In the tables given hereinafter, "SF-1293" means monosodium salt of SF-1293 substance.

TABLE 3

| | | Damage Scale | | | | | | Scale of Regrowth Suppression | |
|---|---|---|---|---|---|---|---|---|---|
| | | 7 Days | | 14 Days | | 1 Month | | | |
| Test Plants | Growth Stage (cm) | SF-1293 (Na salt) | Glyphosate (isopropyl-amine salt) | SF-1293 (Na salt) | Glyphosate (isopropyl-amine salt) | SF-1293 (Na salt) | | Glyphosate (isopropyl-amine salt) | |
| | | 0.1% 0.2 | 0.1 0.2 | 0.1 0.2 | 0.1 0.2 | 0.1 | 0.2 | 0.1 | 0.2 |
| Pc | 100 | 4 5 | 1 2 | 4 5 | 2 3.5 | − | − | + | ± |
| Ht | 70 | 4.5 5 | 3 4 | 5 5 | 4 5 | − | − | − | − |
| Ap | 50 | 5 5 | 3 4.5 | 5 5 | 3 4.5 | − | − | − | − |
| Cy | 30 | 4 5 | 1 2 | 5 5 | 1 2 | − | − | + | + |
| Ro | 30 | 4 5 | 1 2 | 5 5 | 2 3 | − | − | + | + |
| Ic | 80 | 4 5 | 1 1.5 | 5 5 | 1.5 3 | − | − | + | − |
| Pr | 5m | 4 5 | 2 3 | 5 5 | 3 4 | − | − | − | − |
| Ms | 120 | 4 5 | 0.5 1 | 4 5 | 2 3.5 | − | − | + | − |

The names of the test plants are assigned as follows:
Pc: *Pleioblastus chino*
Ht: *Helianthus tuberosus*
Ap: *Artemisia princeps*
Cy: *Cayratia japonica*
Ro: *Rumex obtusifolius*
Ic: *Imperata cyrindrica*
Pr: *Pueraria lobata*
Ms: *Miscanthus sinensis*

As seen from Table 3, application of 150 l/10a of a solution containing SF-1293 substance at a concentration of 0.1–0.2% to spontaneous perennial weeds at the growing stage achieved complete kill thereof irrespective of weed species as well as complete suppression of regrowth.

EXAMPLE 7

Aqueous solutions containing sodium salt of SF-1293 substance at different concentrations indicated in Table 4 below and 0.1% of octylphenylpolyoxyethanol as surfactant were applied at a rate of 150 l/10a to the area where various bushes were spontaneously growing. One month after foliage treatment, damage to plants was visually assessed on a scale of 0 to 5 where 0 signifies no effect and 5 signifies complete kill as described in Example 6.

The results are set out in Table 4.

TABLE 4

| Test Compounds | Concentration | Overall Evaluation | Sc | Ct | Rb | Zp | Pa | Vb |
|---|---|---|---|---|---|---|---|---|
| SF-1293 (Na salt) | 0.1% | 4 | 4 | 4 | 5 | 4 | 4 | 4 |
| SF-1293 (Na salt) | 0.2 | 5 | 5 | 5 | 5 | 5 | 5 | 5 |
| SF-1293 (Na salt) | 0.3 | 5 | 5 | 5 | 5 | 5 | 5 | 5 |
| Glyphosate (isopropyl-amine salt) | 0.1 | 2 | 1.5 | 0.5 | 1 | 0 | 3 | 2 |
| Glyphosate (isopropyl-amine salt) | 0.2 | 3 | 4 | 0.5 | 1.5 | 1 | 4 | 3 |
| Glyphosate (isopropyl-amine salt) | 0.3 | 4 | 4.5 | 1.5 | 2 | 2 | 4.5 | 3.5 |
| Untreated | | 0 | 0 | 0 | 0 | 0 | 0 | 0 |

The names of the plant species are assigned as follows:
Sc: *Smilax china*
Ct: *Castanea crenata*
Rb: *Rubus palmatus*
Zp: *Zanthoxylum piperitum*
Pa: *Pteridium aquilinum*
Vb: *Viburnum dilatatum*

Table 4 shows that SF-1293 substance also exhibits a high herbicidal activity against woody plants irrespective of plant species.

EXAMPLE 8

Aqueous solutions containing sodium salt of SF-1293 substance at different concentrations indicated in Table 5 below and 0.1% of octylphenylpolyoxyethanol as surfactant were applied at a rate of 150 l/10a to woody plants of about 60–70 cm in height. 7 Days and 14 days after treatment, damage to test plants was visually assessed on the same scale (0 to 5) as stated in Example 7. The results are tabulated in Table 5.

TABLE 5

| Test Compounds | Concentration | Damage Scale | | | | | | | | | |
|---|---|---|---|---|---|---|---|---|---|---|---|
| | | 7 Days | | | | | 14 Days | | | | |
| | | Pd | La | Ch | Cp | Ct | Pd | La | Ch | Cp | Ct |
| SF-1293 (Na salt) | 0.125% | 3.5 | 4.5 | 0 | 0 | 5 | 5 | 5 | 0 | 0 | 5 |
| SF-1293 (Na salt) | 0.25% | 4 | 4.5 | 0 | 0.5 | 5 | 5 | 5 | 0 | 1 | 5 |
| SF-1293 (Na salt) | 0.5% | 4 | 4.5 | 0 | 0.5 | 5 | 5 | 5 | 0 | 2 | 5 |
| Glyphosate isopropylamine salt | 0.125% | 0 | 1 | 0 | 0 | 2 | 2 | 2 | 1 | 1 | 3 |
| Glyphosate isopropylamine salt | 0.25% | 1 | 1 | 0 | 1 | 2 | 3 | 3 | 3 | 3 | 4 |
| Glyphosate isopropylaine salt | 0.5% | 2 | 2 | 1 | 2 | 3 | 4 | 4 | 4 | 5 | 5 |
| Untreated | | 0 | 0 | 0 | 0 | 0 | 0 | 0 | 0 | 0 | 0 |

The names of the test plants are assigned as follows:
Pd: *Picea densiflora*
La: *Larix leptolepis*
Ch: *Chamaecyparis obtusa*
Cp: *Cryptomeria japonica*
Ct: *Castanea crenata*

As is observed from Table 5, SF-1293 substance is non-phytotoxic towards *Chamaecyparis obtusa* even upon the application of 150 l/10a of a solution containing the SF-1293 at a concentration of 0.5%, and thus it can be used to selectively control weeds and bushes in the forestry area of the useful plant.

Examples 9-10 illustrate the synergistic effects achieved by the combined use of the SF-1293 substances (A) and the herbicidal urea derivative (B) of formula (II), as well as the herbicidal effects of the SF-1293 substances used alone.

EXAMPLE 9

Aqueous solutions containing the SF-1293 substance (A) and Linuron, the component (B), in admixture or separately, at different concentrations indicated in Table 6 below were applied at a rate of 100 l per 10 ares to *Rumex obtusifolius* (abbreviated as Ro) and one of graminaceous perennial weeds, *Zoysia japonica* (abbreviated as Zy) which had been transplanted into pots at certain growth stage and taken root firmly in the pots. 21 Days after foliage treatment, damage to plants was visually assessed on a scale of 0 to 5 where 0 is no effect and 5 is complete kill as described in Example 6. 3 Months later, further assessment was made for suppression of regrowth based on the degree of killing the under-ground segments which is expressed in terms of symbols ranging from (−) to (+++) where (−) means complete suppression of regrowth and (+++) means maximum regrowth observed as described in Example 6.

The results are set forth in Table 6, where monosodium salt of SF-1293 substance is abbreviated as "SF".

TABLE 6

| Test Compounds Concentration in % | Scales | | | |
|---|---|---|---|---|
| | 21 Days later | | 3 Months later | |
| | Ro | Zy | Ro | Zy |
| SF (0.05%) | 2.5 | 1.5 | +++ | +++ |

TABLE 6-continued

| Test Compounds Concentration in % | Scales | | | |
|---|---|---|---|---|
| | 21 Days later | | 3 Months later | |
| | Ro | Zy | Ro | Zy |
| SF (0.1%) | 3.5 | 2.5 | +++ | +++ |
| Linuron (0.1%) | 3 | 2 | +++ | +++ |
| Linuron (0.3%) | 4 | 4 | +++ | +++ |
| Linuron (0.1%) + SF (0.05%) | 5 | 4 | ++ | + |
| Linuron (0.1%) + SF (0.05%) | 5 | 5 | + | + |
| Linuron (0.3%) + SF (0.05%) | 5 | 5 | − | ± |
| Linuron (0.3%) + SF (0.1%) | 5 | 5 | − | − |
| Untreated | 0 | 0 | +++ | +++ |

Table 6 shows that when the SF-1293 substance (A) or Linuron (B) is applied alone separately to *Rumex obtusifolius* and *Zoysia japonica*, there is obtained substantial damage of foliage of these weeds but little suppression of regrowth of these weeds from their underground roots, and that the combined use of the two components (A) and (B) can achieve complete suppression of such regrowth.

EXAMPLE 10

This example demonstrates that evidently the combined use of the SF-1293 substance (A) and one herbicidal urea derivative (B) selected from N-(3,4-dichlorophenyl)-N'-methoxy-N'-methylurea (i.e., Linuron), N-(3,4-dichlorophenyl)-N',N'-dimethylurea (i.e., Diuron), N-(4-chlorophenyl)-N',N'-dimethylurea (i.e., Monuron), and N-(4-chlorophenyl)-N'-methoxy-N'-methylurea (i.e., Monolinuron), achieves synergistic herbicidal activity, as estimated according to such procedure that the mixture of SF-1293 substance and one of Linuron, Diuron, Monuron and Monolinuron was compared with each single component herbicide in such a manner that the herbicidal data for each component herbicide of said mixture as applied separately at a rate of application equal to that applied via the mixture is compared with the herbicidal data as obtained at the total rate of the component herbicides applied together via the mixture.

Thus, aqueous solutions containing SF-1293 substance (as mono-sodium salt) at different concentrations and 0.1% by weight of octylphenylpolyoxyethanol as the sticking agent; aqueous solutions containing Linuron, Diuron, Monuron or Monolinuron at different concentrations and 0.1% by weight of octylphenylpolyoxyethanol as the sticking agent; and aqueous solutions containing the mixture of SF-1293 substance (mono-sodium salt) and one of Linuron, Diuron, Monuron and Monolinuron at different concentrations together with 0.1% by weight of octylphenylpolyoxyethanol as the sticking agent were prepared. The concentrations of SF-1293 substance and/or the herbicidal urea derivative (namely, Linuron, Diuron, Monuron or Monolinuron) in each of these aqueous solutions prepared were so adjusted that spraying of 5 liters per are of the aqueous solution gave the rate of application of the active ingredient compound as indicated in Tables 7 and 8 shown below.

The aqueous solutions prepared were sprayed onto the foliage of weeds grown in the field and as indicated in Tables 7 and 8.

The weeds under test include the following:
Crab grass (*Digitaria abscendens*) of 30–40 cm in grass height;

Pigweed (*Amaranthus ascendens*) of 30–40 cm in grass height;
Yellow foxtail (*Setaria viridis*) of 30–40 cm in grass height;
Orchard grass (*Dactylis glomerata L.*) of 30–40 cm in grass height;
Smart weed (*Polygonum nodosum*) of 30–40 cm in grass height;
White clover (*Trifolium repenol L.*) of about 20 cm in grass height; and
Bitter dock (*Rumex obtusifolius*) of 30–40 cm in grass height.

20 Days and 40 Days after the foliage treatment, the damage to weeds was assessed by estimating the rate of kill in percentage (0%=No kill, 100%=Complete kill). The test results obtained are tabulated in Tables 7 and 8 below.

TABLE 7

(Herbicidal results estimated 20 Days after Foliage Treatment)

| Test Compounds (Components (A) + (B) and rates of application of the compounds (g/are, active ingredient) | Weight ratio of (A) to (B) components | Kill Rate (%) | | | | | | |
|---|---|---|---|---|---|---|---|---|
| | | Crab grass | Pigweed | Yellow foxtail | Orchard grass | Smart weed | White clover | Bitter dock |
| 5 g/a of SF-1293 | — | 15 | 20 | 20 | 15 | 20 | 20 | 15 |
| 10 g/a of SF-1293 | — | 30 | 35 | 35 | 30 | 35 | 35 | 30 |
| 15 g/a of SF-1293 | — | 50 | 55 | 55 | 50 | 55 | 55 | 50 |
| 20 g/a of SF-1293 | — | 75 | 80 | 80 | 75 | 80 | 80 | 75 |
| 5 g/a of Linuron | — | 10 | 15 | 15 | 10 | 15 | 15 | 10 |
| 10 g/a of Linuron | — | 20 | 25 | 25 | 20 | 25 | 25 | 20 |
| 15 g/a of Linuron | — | 35 | 40 | 40 | 35 | 40 | 40 | 35 |
| 20 g/a of Linuron | — | 50 | 55 | 55 | 50 | 55 | 55 | 50 |
| 5 g/a of SF-1293 + 15 g/a of Linuron | 1:3 | 95 | 100 | 100 | 95 | 100 | 100 | 95 |
| 10 g/a of SF-1293 + 10 g/a of Linuron | 1:1 | 100 | 100 | 100 | 100 | 100 | 100 | 100 |
| 15 g/a of SF-1293 + 5 g/a of Linuron | 3:1 | 90 | 95 | 95 | 90 | 95 | 95 | 90 |
| 5 g/a of Diuron | — | 5 | 10 | 10 | 5 | 10 | 10 | 5 |
| 10 g/a of Diuron | — | 15 | 20 | 20 | 15 | 20 | 20 | 15 |
| 15 g/a of Diuron | — | 30 | 35 | 35 | 30 | 35 | 35 | 30 |
| 20 g/a of Diuron | — | 45 | 50 | 50 | 45 | 50 | 50 | 45 |
| 5 g/a of SF-1293 + 15 g/a of Diuron | 1:3 | 90 | 95 | 95 | 90 | 95 | 95 | |
| 10 g/a of SF-1293 + 10 g/a of Diuron | 1:1 | 100 | 100 | 100 | 100 | 100 | 100 | 100 |
| 15 g/a of SF-1293 + 5 g/a of Diuron | 3:1 | 85 | 90 | 90 | 85 | 90 | 90 | |
| 5 g/a of Monuron | — | 5 | 10 | 10 | 5 | 10 | 10 | 5 |
| 10 g/a of Monuron | — | 15 | 20 | 20 | 15 | 20 | 20 | 15 |
| 15 g/a of Monuron | — | 30 | 35 | 35 | 30 | 35 | 35 | 30 |
| 20 g/a of Monuron | — | 45 | 50 | 50 | 45 | 50 | 50 | 45 |
| 5 g/a of SF-1293 + 15 g/a of Monuron | 1:3 | 90 | 95 | 95 | 90 | 95 | 95 | 90 |
| 10 g/a of SF-1293 + 10 g/a of Monuron | 1:1 | 100 | 100 | 100 | 100 | 100 | 100 | 100 |
| 15 g/a of SF-1293 + 5 g/a of Monuron | 3:1 | 85 | 90 | 90 | 85 | 90 | 90 | 85 |
| 5 g/a of Monolinuron | — | 15 | 10 | 10 | 5 | 10 | 10 | 5 |
| 10 g/a of Monolinuron | — | 15 | 20 | 20 | 15 | 20 | 20 | 15 |
| 15 g/a of Monolinuron | — | 30 | 35 | 35 | 30 | 35 | 35 | 30 |
| 20 g/a of Monolinuron | — | 45 | 50 | 50 | 45 | 50 | 50 | 45 |
| 5 g/a of SF-1293 + 15 g/a of Monolinuron | 1:3 | 90 | 95 | 95 | 90 | 95 | 95 | 90 |
| 10 g/a of SF-1293 + 10 g/a of Monolinuron | 1:1 | 100 | 100 | 100 | 100 | 100 | 100 | 100 |
| 15 g/a of SF-1293 + 5 g/a of Monolinuron | 3:1 | 85 | 90 | 90 | 85 | 90 | 90 | 85 |
| Untreated (Control) | | 0 | 0 | 0 | 0 | 0 | 0 | 0 |

TABLE 8

(Herbicidal results estimated 40 Days after Foliage Treatment)

| Test Compounds (Components (A) + (B) and rates of application of the compounds (g/are, active ingredient) | Weight ratio of (A) to (B) components | Kill Rate (%) | | | | | | |
|---|---|---|---|---|---|---|---|---|
| | | Crab grass | Pigweed | Yellow foxtail | Orchard grass | Smart weed | White clover | Bitter dock |
| 5 g/a of SF-1293 | — | 5 | 10 | 10 | 5 | 10 | 5 | 5 |
| 10 g/a of SF-1293 | — | 20 | 25 | 25 | 20 | 25 | 20 | 20 |
| 15 g/a of SF-1293 | — | 40 | 45 | 45 | 40 | 45 | 40 | 40 |
| 20 g/a of SF-1293 | — | 65 | 70 | 70 | 65 | 70 | 70 | 65 |
| 5 g/a of Linuron | — | 5 | 10 | 10 | 5 | 10 | 5 | 5 |
| 10 g/a of Linuron | — | 15 | 20 | 20 | 15 | 20 | 15 | 15 |
| 15 g/a of Linuron | — | 30 | 35 | 35 | 30 | 35 | 30 | 30 |
| 20 g/a of Linuron | — | 45 | 50 | 50 | 45 | 50 | 45 | 45 |
| 5 g/a of SF-1293 + 15 g/a of Linuron | 1:3 | 100 | 100 | 100 | 100 | 100 | 100 | 100 |

TABLE 8-continued (Herbicidal results estimated 40 Days after Foliage Treatment)

| Test Compounds (Components (A) + (B) and rates of application of the compounds (g/are, active ingredient) | Weight ratio of (A) to (B) components | Kill Rate (%) | | | | | | |
|---|---|---|---|---|---|---|---|---|
| | | Crab grass | Pigweed | Yellow foxtail | Orchard grass | Smart weed | White clover | Bitter dock |
| 10 g/a of SF-1293 + 10 g/a of Linuron | 1:1 | 100 | 100 | 100 | 100 | 100 | 100 | 100 |
| 15 g/a of SF-1293 + 5 g/a of Linuron | 3:1 | 95 | 100 | 100 | 95 | 100 | 100 | 95 |
| 5 g/a of Diuron | — | 0 | 5 | 5 | 0 | 5 | 0 | 0 |
| 10 g/a of Diuron | — | 10 | 15 | 15 | 10 | 15 | 10 | 10 |
| 15 g/a of Diuron | — | 25 | 30 | 30 | 25 | 30 | 25 | 25 |
| 20 g/a of Diuron | — | 40 | 45 | 45 | 40 | 45 | 40 | 40 |
| 5 g/a of SF-1293 + 15 g/a of Diuron | 1:3 | 95 | 100 | 100 | 95 | 100 | 95 | 95 |
| 10 g/a of SF-1293 + 10 g/a of Diuron | 1:1 | 100 | 100 | 100 | 100 | 100 | 100 | 100 |
| 15 g/a of SF-1293 + 5 g/a of Diuron | 3:1 | 90 | 95 | 95 | 90 | 95 | 90 | 90 |
| 5 g/a of Monuron | — | 0 | 5 | 5 | 0 | 5 | 0 | 0 |
| 10 g/a of Monuron | — | 10 | 15 | 15 | 10 | 15 | 10 | 10 |
| 15 g/a of Monuron | — | 25 | 30 | 30 | 25 | 30 | 25 | 25 |
| 20 g/a of Monuron | — | 40 | 45 | 45 | 40 | 45 | 40 | 40 |
| 5 g/a of SF-1293 + 15 g/a of Monuron | 1:3 | 95 | 100 | 100 | 95 | 100 | 95 | 95 |
| 10 g/a of SF-1293 + 10 g/a of Monuron | 1:1 | 100 | 100 | 100 | 100 | 100 | 100 | 100 |
| 15 g/a of SF-1293 + 5 g/a of Monuron | 3:1 | 90 | 95 | 95 | 90 | 95 | 90 | 90 |
| 5 g/a of Monolinuron | — | 0 | 5 | 5 | 0 | 5 | 0 | 0 |
| 10 g/a of Monolinuron | — | 10 | 15 | 15 | 10 | 15 | 10 | 10 |
| 15 g/a of Monolinuron | — | 25 | 30 | 30 | 25 | 30 | 25 | 25 |
| 20 g/a of Monolinuron | — | 40 | 45 | 45 | 40 | 45 | 40 | 40 |
| 5 g/a of SF-1293 + 15 g/a of Monolinuron | 1:3 | 95 | 100 | 100 | 95 | 100 | 95 | 95 |
| 10 g/a of SF-1293 + 10 g/a of Monolinuron | 1:1 | 100 | 100 | 100 | 100 | 100 | 100 | 100 |
| 15 g/a of SF-1293 + 5 g/a of Monolinuron | 3:1 | 90 | 95 | 95 | 95 | 95 | 90 | 90 |
| Untreated (Control) | | 0 | 0 | 0 | 0 | 0 | 0 | 0 |

The herbicidal results of Tables 7 and 8 have revealed that the combined use of SF-1293 substance (sodium salt) and Linuron, Diuron, Monuron or Monolinuron exhibits a herbicidal effect which is significantly greater than the mere total of the effects obtained from the use of the individual component compounds alone, so that the synergism have been attained through the combined use of SF-1293 substance (sodium salt) and one of Linuron, Diuron, Monuron and Monolinuron.

What we claim is:

1. A process for severely damaging or killing unwanted herbaceous and bushy plants, which comprises applying to unwanted herbaceous plants or the growth medium of said plants a composition consisting essentially of (A) SF-1293 substance or a salt thereof selected from the group consisting of sodium, potassium, lithium and ammonium salts thereof and (B) N-(3,4-dichlorophenyl)-N'-methoxy-N'-methylurea, at a weight ratio of the component (A) to component (B) in the range of 3:1 to 1:3 and at the rate of application of the component (A) in the range of 50 to 150 g per 10 ares, to inhibit the growth of said unwanted plant.

2. A process according to claim 1 in which the weight ratio of component (A) to component (B) is in the range of 3:1 to 1:1.

3. A process according to claim 1 wherein component (A) is the sodium salt of SF-1293 substance.

4. A process for severely damaging or killing unwanted herbaceous and bushy plants, which comprises applying to unwanted herbaceous plants or the growth medium of said plants a composition consisting essentially of (A) SF-1293 substance or a salt thereof selected from the group consisting of sodium, potassium, lithium and ammonium salts thereof and (B) N-(4-chlorophenyl)-N'-methoxy-N'-methylurea, at a weight ratio of the component (A) to component (B) in the range of 3:1 to 1:3 and at a rate of application of component (A) in the range of 50 to 120 g per 10 ares, to inhibit the growth of said unwanted plant.

5. A process for severely damaging or killing unwanted herbaceous and bushy plants, which comprises applying to unwanted herbaceous plants or the growth medium of said plants a composition consisting essentially of (A) SF-1293 substance or a salt thereof selected from the group consisting of sodium, potassium, lithium and ammonium salts thereof and (B) N-(4-chlorophenyl)-N',N'-dimethylurea, at a weight ratio of the component (A) to component (B) in the range of 3:1 to 1:3 and at the rate of application of component (A) in the range of 50 to 150 g per 10 ares, to inhibit the growth of said unwanted plant.

6. A process for severely damaging or killing unwanted herbaceous and bushy plants, which comprises applying to unwanted herbaceous plants or the growth medium of said plants a composition consisting essentially of (A) SF-1293 substance or a salt thereof selected from the group consisting of sodium, potassium, lithium and ammonium salts thereof and (B) N-(3,4-di-chlorophenyl)-N',N'-dimethylurea, at a weight ratio of the component (A) to component (B) in the range of 3:1 to 1:3 and at the rate of application of component (A) in the range of 50 to 150 g per 10 ares, to inhibit the growth of said unwanted plant.

* * * * *